United States Patent
Twomey et al.

(10) Patent No.: US 10,828,756 B2
(45) Date of Patent: Nov. 10, 2020

(54) DISASSEMBLY METHODS FACILITATING REPROCESSING OF MULTI-FUNCTION SURGICAL INSTRUMENTS

(71) Applicant: COVIDIEN LP, Mansfield, MA (US)

(72) Inventors: John R. Twomey, Longmont, CO (US); James D. Allen, IV, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 130 days.

(21) Appl. No.: 15/960,816

(22) Filed: Apr. 24, 2018

(65) Prior Publication Data
US 2019/0321950 A1    Oct. 24, 2019

(51) Int. Cl.
| B23P 19/02 | (2006.01) |
| B25B 27/02 | (2006.01) |
| A61B 18/14 | (2006.01) |
| A61B 18/12 | (2006.01) |

(52) U.S. Cl.
CPC .......... *B25B 27/02* (2013.01); *A61B 18/1206* (2013.01); *A61B 18/1445* (2013.01); *B23P 19/025* (2013.01)

(58) Field of Classification Search
CPC ..... B25B 27/02; B25B 27/20; A61B 18/1206; A61B 18/1445; A61B 2090/0813; A61B 2018/1475; A61B 2018/1455; A61B 2018/1422; B23P 19/025; G05G 1/085; E05F 11/382
See application file for complete search history.

(56) References Cited

U.S. PATENT DOCUMENTS

| 4,005,714 | A | 2/1977 | Hiltebrandt |
| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |

(Continued)

FOREIGN PATENT DOCUMENTS

| AU | 2011253698 A1 | 12/2011 |
| AU | 2013205789 A1 | 1/2014 |

(Continued)

OTHER PUBLICATIONS

"How I Do It" KD Tool # 435 Tool for Window Crank and Door Handle http://chrysler300club.com/how/crank/crank1.html (Year: 2011).*

*Primary Examiner* — Sarang Afzali
*Assistant Examiner* — Ruth G Hidalgo-Hernandez
(74) *Attorney, Agent, or Firm* — Carter, DeLuca & Farrell LLP

(57) ABSTRACT

A method of disassembling a surgical instrument includes obtaining a surgical instrument including a housing, an input shaft defining an axis and extending from the housing, and a paddle engaged with the input shaft and configured to pivot about the axis. The method further includes disengaging a cover plate of the paddle from a body of the paddle by providing a force to the cover plate substantially in a direction parallel to the axis and disengaging the body from the input shaft by providing a force to the body substantially in a direction parallel to the axis.

8 Claims, 9 Drawing Sheets

(56) References Cited

U.S. PATENT DOCUMENTS

| | | |
|---|---|---|
| 5,026,379 A | 6/1991 | Yoon |
| D343,453 S | 1/1994 | Noda |
| 5,312,391 A | 5/1994 | Wilk |
| 5,318,589 A | 6/1994 | Lichtman |
| 5,324,254 A | 6/1994 | Phillips |
| D348,930 S | 7/1994 | Olson |
| D349,341 S | 8/1994 | Lichtman et al. |
| 5,342,359 A | 8/1994 | Rydell |
| 5,368,600 A | 11/1994 | Failla et al. |
| D354,564 S | 1/1995 | Medema |
| 5,401,274 A | 3/1995 | Kusunoki |
| D358,887 S | 5/1995 | Feinberg |
| 5,411,519 A | 5/1995 | Tovey et al. |
| 5,445,638 A | 8/1995 | Rydell et al. |
| 5,458,598 A | 10/1995 | Feinberg et al. |
| 5,527,313 A | 6/1996 | Scott et al. |
| 5,556,397 A | 9/1996 | Long et al. |
| 5,611,813 A | 3/1997 | Lichtman |
| D384,413 S | 9/1997 | Zlock et al. |
| 5,735,873 A | 4/1998 | MacLean |
| H1745 H | 8/1998 | Paraschac |
| 5,792,164 A | 8/1998 | Lakatos et al. |
| 5,807,393 A | 9/1998 | Williamson, IV et al. |
| D402,028 S | 12/1998 | Grimm et al. |
| D408,018 S | 4/1999 | McNaughton |
| 5,893,863 A | 4/1999 | Yoon |
| 5,919,202 A | 7/1999 | Yoon |
| D416,089 S | 11/1999 | Barton et al. |
| 6,004,319 A | 12/1999 | Goble et al. |
| D424,694 S | 5/2000 | Tetzlaff et al. |
| D425,201 S | 5/2000 | Tetzlaff et al. |
| 6,113,596 A | 9/2000 | Hooven et al. |
| H1904 H | 10/2000 | Yates et al. |
| 6,156,009 A | 12/2000 | Grabek |
| 6,190,386 B1 | 2/2001 | Rydell |
| 6,270,497 B1 | 8/2001 | Sekino et al. |
| D449,886 S | 10/2001 | Tetzlaff et al. |
| 6,299,625 B1 | 10/2001 | Bacher |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,387,094 B1 | 5/2002 | Eitenmuller |
| H2037 H | 7/2002 | Yates et al. |
| D465,281 S | 11/2002 | Lang |
| D466,209 S | 11/2002 | Bon |
| 6,551,313 B1 | 4/2003 | Levin |
| 6,558,385 B1 | 5/2003 | McClurken et al. |
| 6,679,882 B1 | 1/2004 | Komerup |
| D493,888 S | 8/2004 | Reschke |
| D496,997 S | 10/2004 | Dycus et al. |
| 6,808,525 B2 | 10/2004 | Latterell et al. |
| D499,181 S | 11/2004 | Dycus et al. |
| 6,837,888 B2 | 1/2005 | Ciarrocca et al. |
| D502,994 S | 3/2005 | Blake, III |
| D509,297 S | 9/2005 | Wells |
| 6,942,662 B2 | 9/2005 | Goble et al. |
| 7,033,356 B2 | 4/2006 | Latterell et al. |
| 7,063,699 B2 | 6/2006 | Hess et al. |
| D525,361 S | 7/2006 | Hushka |
| D531,311 S | 10/2006 | Guerra et al. |
| 7,128,254 B2 | 10/2006 | Shelton, IV et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| 7,208,005 B2 | 4/2007 | Frecker et al. |
| D541,611 S | 5/2007 | Aglassinger |
| D541,938 S | 5/2007 | Kerr et al. |
| D545,432 S | 6/2007 | Watanabe |
| 7,232,440 B2 | 6/2007 | Dumbauld et al. |
| D547,154 S | 7/2007 | Lee |
| D564,662 S | 3/2008 | Moses et al. |
| D567,943 S | 4/2008 | Moses et al. |
| 7,367,976 B2 | 5/2008 | Lawes et al. |
| 7,402,162 B2 | 7/2008 | Ouchi |
| D575,395 S | 8/2008 | Hushka |
| D575,401 S | 8/2008 | Hixson et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,481,810 B2 | 1/2009 | Dumbauld et al. |
| 7,510,562 B2 | 3/2009 | Lindsay |
| 7,588,570 B2 | 9/2009 | Wakikaido et al. |
| 7,658,311 B2 | 2/2010 | Boudreaux |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,758,577 B2 | 7/2010 | Nobis et al. |
| D621,503 S | 8/2010 | Often et al. |
| 7,789,878 B2 | 9/2010 | Dumbauld et al. |
| 7,815,636 B2 | 10/2010 | Ortiz |
| 7,819,299 B2 | 10/2010 | Shelton, IV et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,879,035 B2 | 2/2011 | Garrison et al. |
| D649,249 S | 11/2011 | Guerra |
| D649,643 S | 11/2011 | Allen, IV et al. |
| D661,394 S | 6/2012 | Romero et al. |
| 8,257,352 B2 | 9/2012 | Lawes et al. |
| 8,333,765 B2 | 12/2012 | Johnson et al. |
| 8,353,437 B2 | 1/2013 | Boudreaux |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,679,140 B2 | 3/2014 | Butcher |
| RE44,834 E | 4/2014 | Dumbauld et al. |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 | 1/2015 | Twomey |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |

(56) References Cited

U.S. PATENT DOCUMENTS

| | | |
|---|---|---|
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,060,780 B2 | 6/2015 | Twomey et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 2002/0049442 A1 | 4/2002 | Roberts et al. |
| 2004/0236326 A1 | 11/2004 | Schulze et al. |
| 2005/0187547 A1 | 8/2005 | Sugi |
| 2006/0129146 A1 | 6/2006 | Dycus et al. |
| 2007/0078458 A1 | 4/2007 | Dumbauld et al. |
| 2007/0106295 A1 | 5/2007 | Garrison et al. |
| 2007/0213707 A1 | 9/2007 | Dumbauld et al. |
| 2007/0278277 A1 | 12/2007 | Wixey et al. |
| 2008/0083813 A1 | 4/2008 | Zemlok et al. |
| 2008/0110958 A1 | 5/2008 | McKenna et al. |
| 2008/0215050 A1 | 9/2008 | Bakos |
| 2008/0243120 A1 | 10/2008 | Lawes et al. |
| 2008/0314954 A1 | 12/2008 | Boudreaux |
| 2009/0012556 A1 | 1/2009 | Boudreaux et al. |
| 2009/0112206 A1 | 4/2009 | Dumbauld et al. |
| 2009/0125026 A1 | 5/2009 | Rioux et al. |
| 2009/0125027 A1 | 5/2009 | Fischer |
| 2009/0131974 A1 | 5/2009 | Pedersen et al. |
| 2009/0171350 A1 | 7/2009 | Dycus et al. |
| 2009/0182327 A1 | 7/2009 | Unger |
| 2009/0254084 A1 | 10/2009 | Naito |
| 2010/0185196 A1 | 7/2010 | Sakao et al. |
| 2010/0185197 A1 | 7/2010 | Sakao et al. |
| 2010/0292690 A1 | 11/2010 | Livneh |
| 2011/0004209 A1 | 1/2011 | Lawes et al. |
| 2011/0071525 A1 | 3/2011 | Dumbauld et al. |
| 2011/0087218 A1 | 4/2011 | Boudreaux et al. |
| 2011/0130757 A1 | 6/2011 | Horne et al. |
| 2011/0264093 A1 | 10/2011 | Schall |
| 2011/0276049 A1 | 11/2011 | Gerhardt |
| 2011/0319886 A1 | 12/2011 | Chojin et al. |
| 2012/0083827 A1 | 4/2012 | Artale et al. |
| 2012/0184988 A1 | 7/2012 | Twomey et al. |
| 2012/0209263 A1 | 8/2012 | Sharp et al. |
| 2012/0239034 A1 | 9/2012 | Horner et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296323 A1 | 11/2012 | Chernov et al. |
| 2012/0296371 A1 | 11/2012 | Kappus et al. |
| 2012/0303026 A1 | 11/2012 | Dycus et al. |
| 2012/0323238 A1 | 12/2012 | Tyrrell et al. |
| 2012/0330308 A1 | 12/2012 | Joseph |
| 2012/0330351 A1 | 12/2012 | Friedman et al. |
| 2013/0018364 A1 | 1/2013 | Chernov et al. |
| 2013/0022495 A1 | 1/2013 | Allen, IV et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0144284 A1 | 6/2013 | Behnke, II et al. |
| 2013/0165907 A1 | 6/2013 | Attar et al. |
| 2013/0197503 A1 | 8/2013 | Orszulak |
| 2013/0218198 A1 | 8/2013 | Larson et al. |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296854 A1 | 11/2013 | Mueller |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |
| 2014/0100564 A1 | 4/2014 | Garrison |
| 2014/0100568 A1 | 4/2014 | Garrison |
| 2014/0135763 A1 | 5/2014 | Kappus et al. |
| 2014/0276797 A1 | 9/2014 | Batchelor et al. |
| 2016/0074101 A1* | 3/2016 | Anglese ............ A61B 18/1445 606/47 |

FOREIGN PATENT DOCUMENTS

| | | |
|---|---|---|
| CN | 201299462 Y | 9/2009 |
| CN | 205181468 U | 4/2016 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 4242143 A1 | 6/1994 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009318 U1 | 8/2007 |
| DE | 202007009317 U1 | 10/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1530952 | 5/2005 |
| EP | 2679176 A1 | 1/2014 |
| JP | 61501068 | 9/1984 |

(56) References Cited

FOREIGN PATENT DOCUMENTS

| | | | |
|---|---|---|---|
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | H0856955 | 5/1996 |
| JP | 08252263 A | 10/1996 |
| JP | 8289895 | 11/1996 |
| JP | 8317934 A | 12/1996 |
| JP | 8317936 A | 12/1996 |
| JP | 09000538 A | 1/1997 |
| JP | H0910223 | 1/1997 |
| JP | 9122138 A | 5/1997 |
| JP | 0010000195 A | 1/1998 |
| JP | 10019884 | 1/1998 |
| JP | H1024051 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 A | 1/2001 |
| JP | 2001029355 | 2/2001 |
| JP | 2001029356 A | 2/2001 |
| JP | 2001003400 | 4/2001 |
| JP | 2001128990 A | 5/2001 |
| JP | 2001190564 A | 7/2001 |
| JP | 2001520543 A | 10/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005144195 A | 6/2005 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| SU | 401367 A1 | 10/1973 |
| WO | 9846150 A1 | 10/1998 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A3 | 4/2006 |
| WO | 2007118608 A1 | 10/2007 |
| WO | 2008040483 A1 | 4/2008 |
| WO | 2011018154 A1 | 2/2011 |

\* cited by examiner

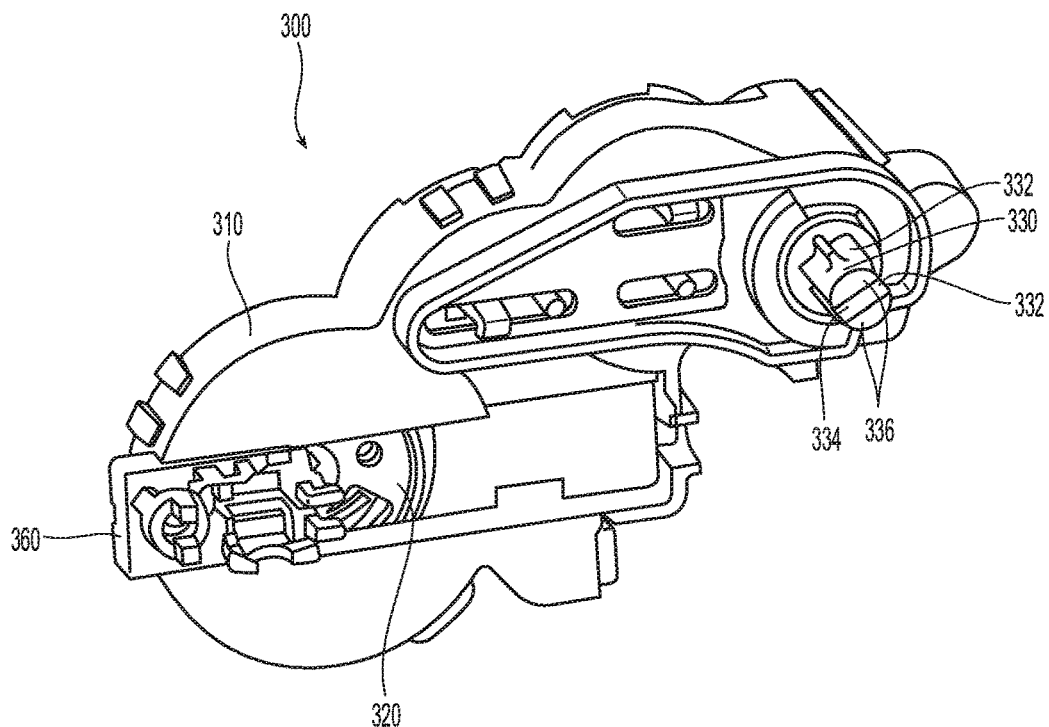
Fig. 5
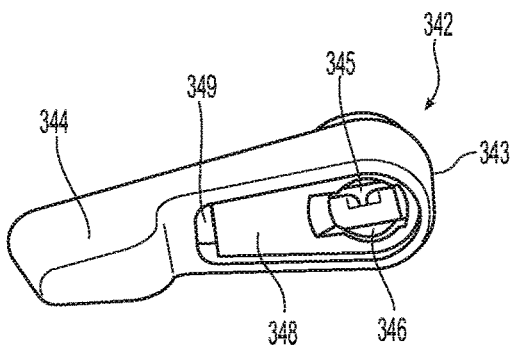
Fig. 6A
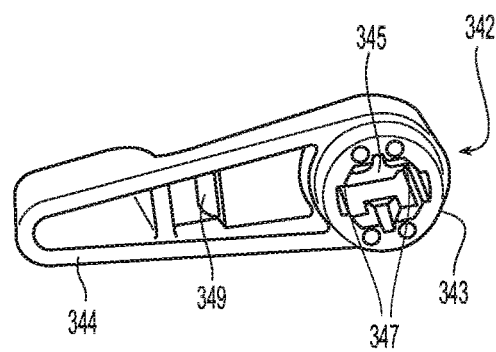
Fig. 6B
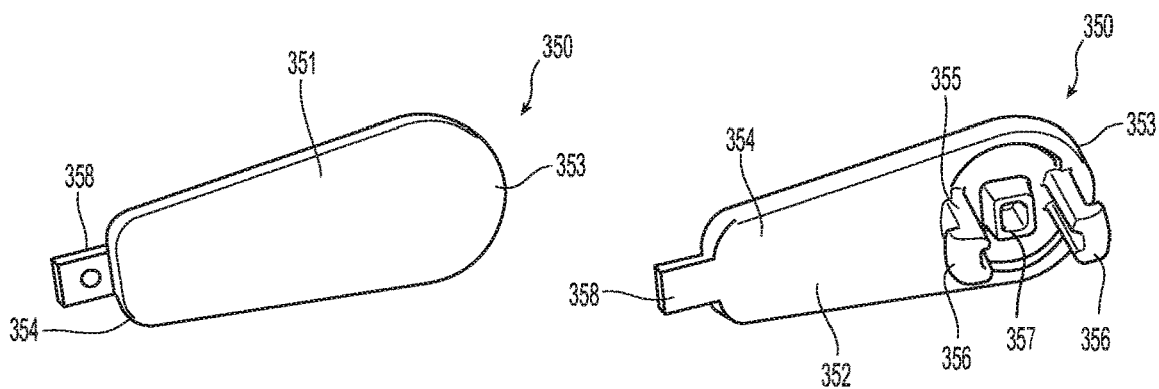
Fig. 7A
Fig. 7B

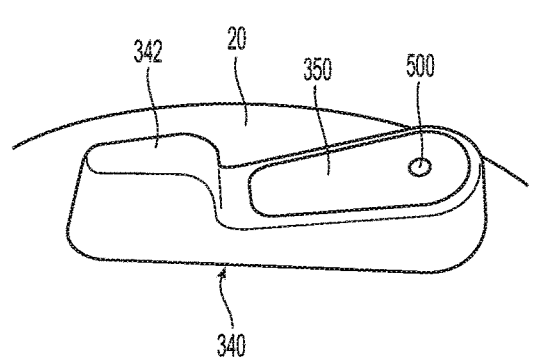
*Fig. 8A*
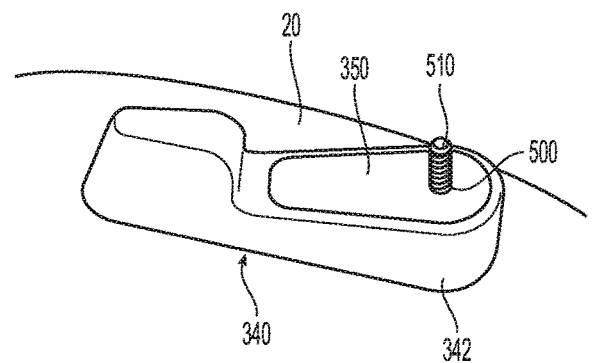
*Fig. 8B*
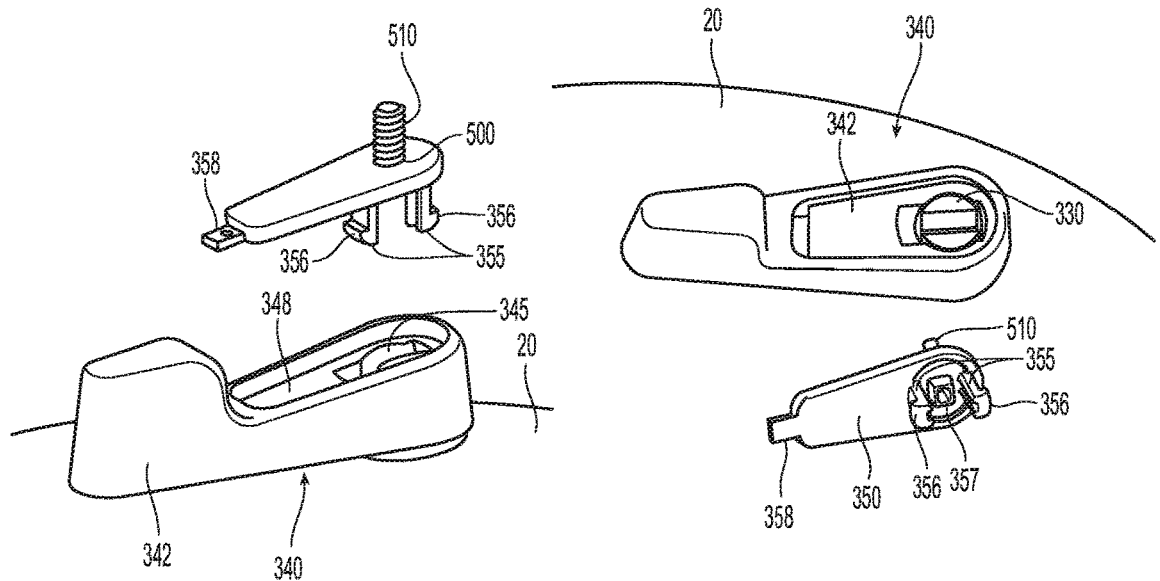
*Fig. 8C*  *Fig. 8D*
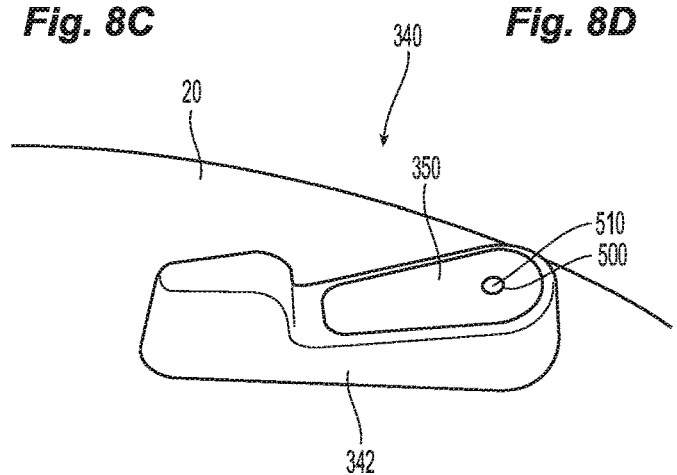
*Fig. 8E*

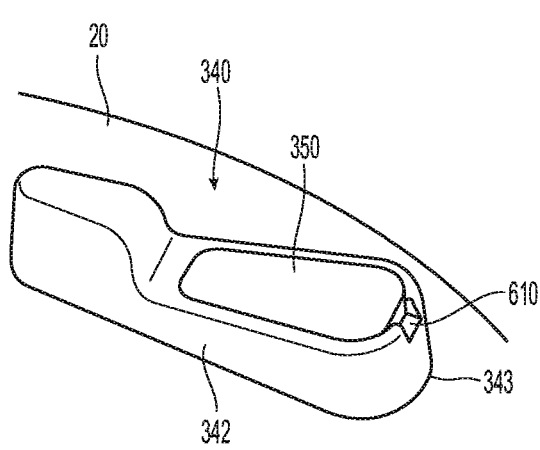 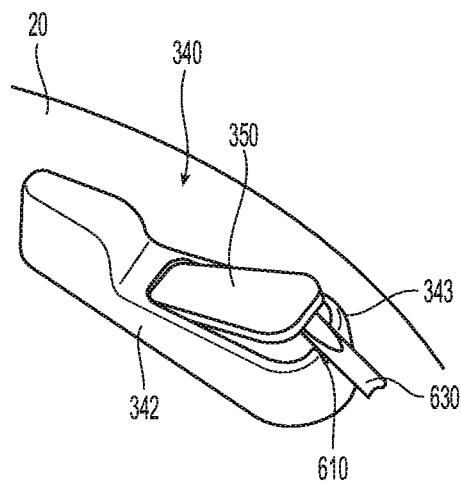
*Fig. 9A*  *Fig. 9B*
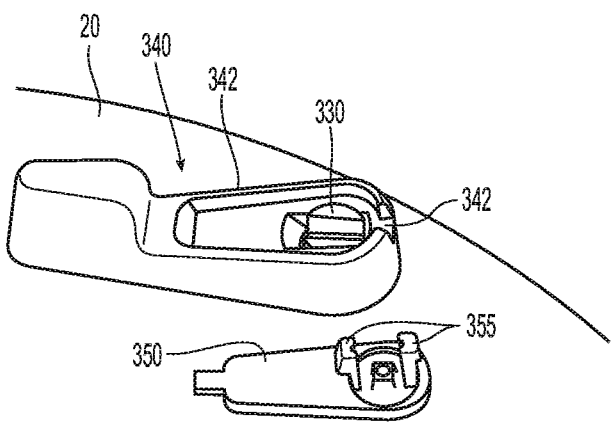
*Fig. 9C*
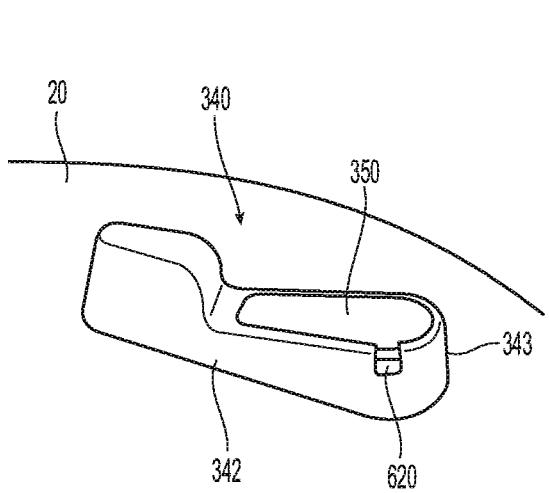 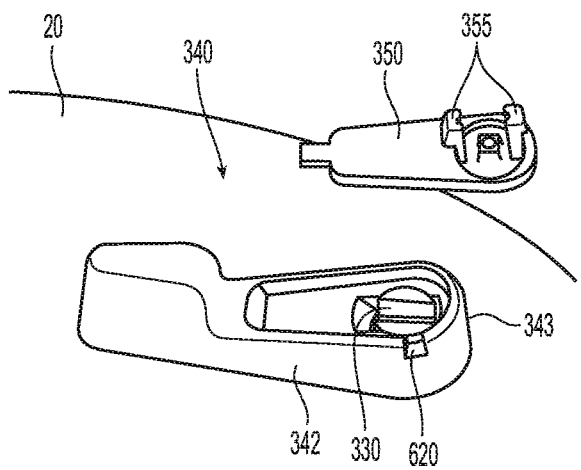
*Fig. 10A*  *Fig. 10B*

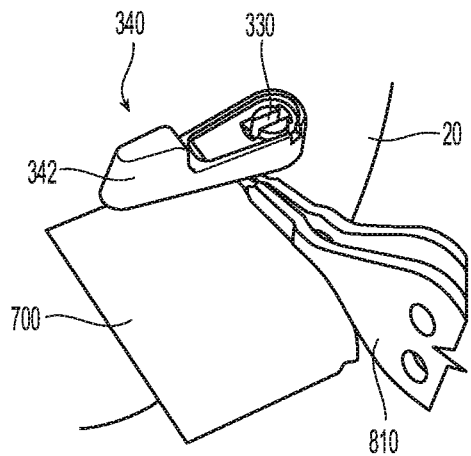
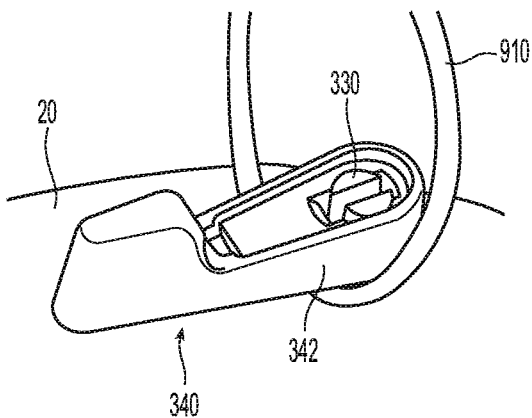
*Fig. 13*     *Fig. 14*
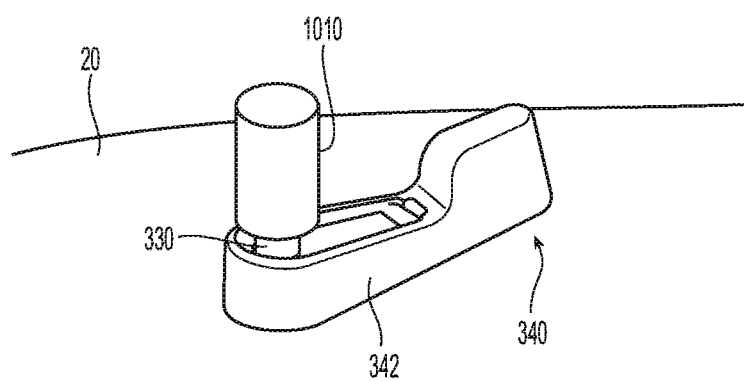
*Fig. 15*

US 10,828,756 B2

DISASSEMBLY METHODS FACILITATING REPROCESSING OF MULTI-FUNCTION SURGICAL INSTRUMENTS

BACKGROUND

Technical Field

The present disclosure relates to multi-function surgical instruments and, more particularly, to disassembly tools and methods facilitating reprocessing of multi-function surgical instruments.

Background of Related Art

Multi-function surgical instruments are beneficial in that they allow multiple surgical tasks to be performed with a single instrument, obviating the need to alternatingly remove and insert different instruments for performing different surgical tasks. However, in order to provide additional functionality, additional components are added that must fit within the spatial and functional constraints of the instrument. As a result, multi-function surgical instruments tend to be relatively complex in their design and manufacture.

Surgical instrument can generally be categorized as reusable instruments (e.g., instruments that are cleaned and/or sterilized), disposable instruments (e.g., instruments that are entirely discarded after a single use), and reposable instruments (e.g., instruments wherein portions are disposable and other portions are reusable after cleaning and/or sterilization). A new class of so called reprocessed instruments has recently been introduced by manufacturers. Typically, these reprocessed instruments are disposable instruments (or reposable instruments) that are collected after a surgical use and returned to a manufacturer where the instruments are disassembled, cleaned/disinfected, refurbished, re-assembled, sterilized and sold as reprocessed instruments. In many cases, most of the original parts of an instrument are re-used to provide the necessary parts for reassembly of the same instrument. Parts that wear during use, are broken during disassembly, and/or are otherwise unable to be reprocessed as-is may be refurbished, modified, and/or alternatively replaced with replacement components.

With respect to reprocessing of certain surgical instruments, such as multi-function surgical instruments, efficient and effective disassembly, cleaning/disinfection, component replacement, component refurbishment, reassembly, and sterilization can be challenging. There is therefore a need for systems and methods facilitating reprocessing of surgical instruments.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is a method of disassembling a surgical instrument. The method includes obtaining a surgical instrument including a housing, an input shaft defining an axis and extending from the housing, and a paddle engaged with the input shaft and configured to pivot about the axis. The method further includes disengaging a cover plate of the paddle from a body of the paddle by providing a force to the cover plate substantially in a direction parallel to the axis and disengaging the body from the input shaft by providing a force to the body substantially in a direction parallel to the axis.

In an aspect of the present disclosure, disengaging the cover plate includes engaging a set screw with the cover plate and manipulating the set screw to provide the force to the cover plate. In such aspects, the set screw may be engaged with the cover plate in alignment with the axis. Additionally or alternatively, engaging the set screw includes drilling a pilot hole through the cover plate and threading the set screw into the pilot hole.

In another aspect of the present disclosure, disengaging the cover plate includes creating a notch in the body adjacent the cover plate, inserting a pry tool into the notch, and providing the force to the cover plate using the pry tool to disengage the cover plate from the body. In such aspects, the notch may be created adjacent the axis.

In still another aspect of the present disclosure, disengaging the body from the input shaft includes inserting a pry tool between the housing and the body adjacent the axis and manipulating the pry tool to provide the force to the body. In such aspects, manipulating the pry tool to provide the force to the body may include rotating the pry tool. Additionally or alternatively, a protective sheet is positioned between the housing and the pry tool to protect the housing during manipulation of the pry tool.

In yet another aspect of the present disclosure, disengaging the body from the input shaft includes inserting a separator tool between the housing and the body adjacent the axis and actuating the separator tool to provide the force to the body.

In still yet another aspect of the present disclosure, disengaging the body from the input shaft includes inserting a lasso loop between the housing and the body adjacent the axis and pulling the lasso loop to provide the force to the body.

In another aspect of the present disclosure, disengaging the body from the input shaft further includes urging arms of the input shaft inwardly prior to providing the force to the body. The arms may be urged inwardly using an insert or a pliers, for example.

In another aspect of the present disclosure, disengaging the body from the input shaft includes engaging a removal tool with the body and actuating a lever of the removal tool to provide the force to the body. Engaging the removal tool with the body may include engaging an inner shaft of the removal tool with the body and/or actuating the lever of the removal tool may including sliding an outer shaft of the removal tool relative to the inner shaft and into contact with the housing to provide the force to the body. Further, the lever of the removal tool may be pivotably coupled to the inner shaft and coupled to the outer shaft via a rack and pinion such that actuating the lever includes pivoting the lever relative to the inner shaft.

In yet another aspect of the present disclosure, the removal tool further includes an insert disposed therein and configured to urge arms of the input shaft inwardly prior to providing the force to the body to facilitate removal of the body from the input shaft.

BRIEF DESCRIPTION OF THE DRAWINGS

Various aspects of the present disclosure are described herein with reference to the drawings wherein like reference numerals identify similar or identical elements and:

FIG. 5 is a perspective view of a gear box of the surgical instrument of FIG. 1;

FIGS. 6A and 6B are front and back perspective views of a body of a deployment paddle of the surgical instrument of FIG. 1;

FIGS. 7A and 7B are front and back perspective views of a cover plate of the deployment paddle of FIGS. 6A and 6B;

FIGS. 8A-8D illustrate tools and/or methods of disassembling the cover plate of the paddle from the body thereof;

FIG. 8E illustrates tools and/or methods of reassembling the cover plate of the paddle with the body thereof;

FIGS. 9A-9C illustrate other tools and/or methods of disassembling the cover plate of the paddle from the body thereof;

FIGS. 10A and 10B illustrate still other tools and/or methods of disassembling the cover plate of the paddle from the body thereof;

FIG. 13 illustrates other tools and/or methods of disassembling the body of the paddle from the surgical instrument of FIG. 1;

FIG. 14 illustrates still other tools and/or methods of disassembling the body of the paddle from the surgical instrument of FIG. 1;

FIG. 15 illustrates yet other tools and/or methods of disassembling the body of the paddle from the surgical instrument of FIG. 1.

DETAILED DESCRIPTION

Figure 1:
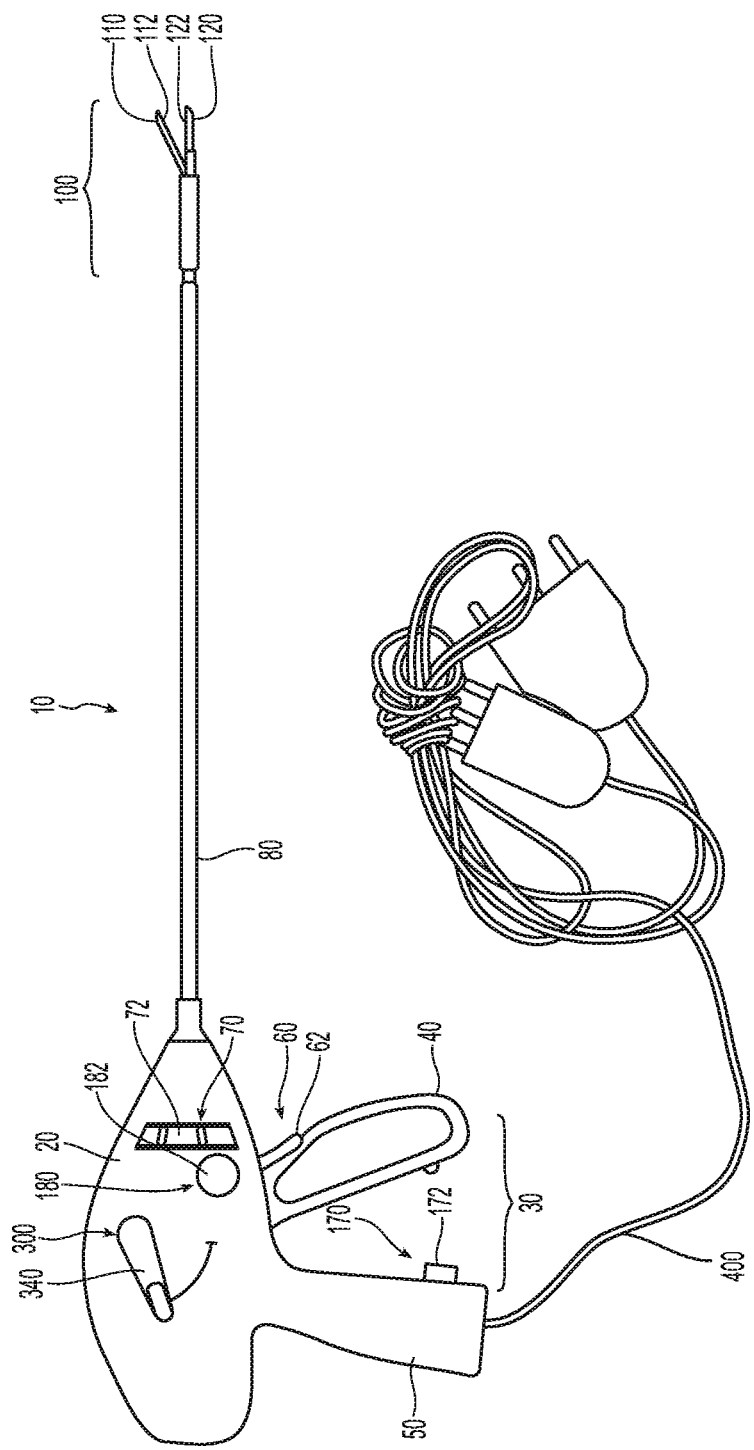
FIG. 1 is a side view of a multi-function surgical instrument.
Figure 2:
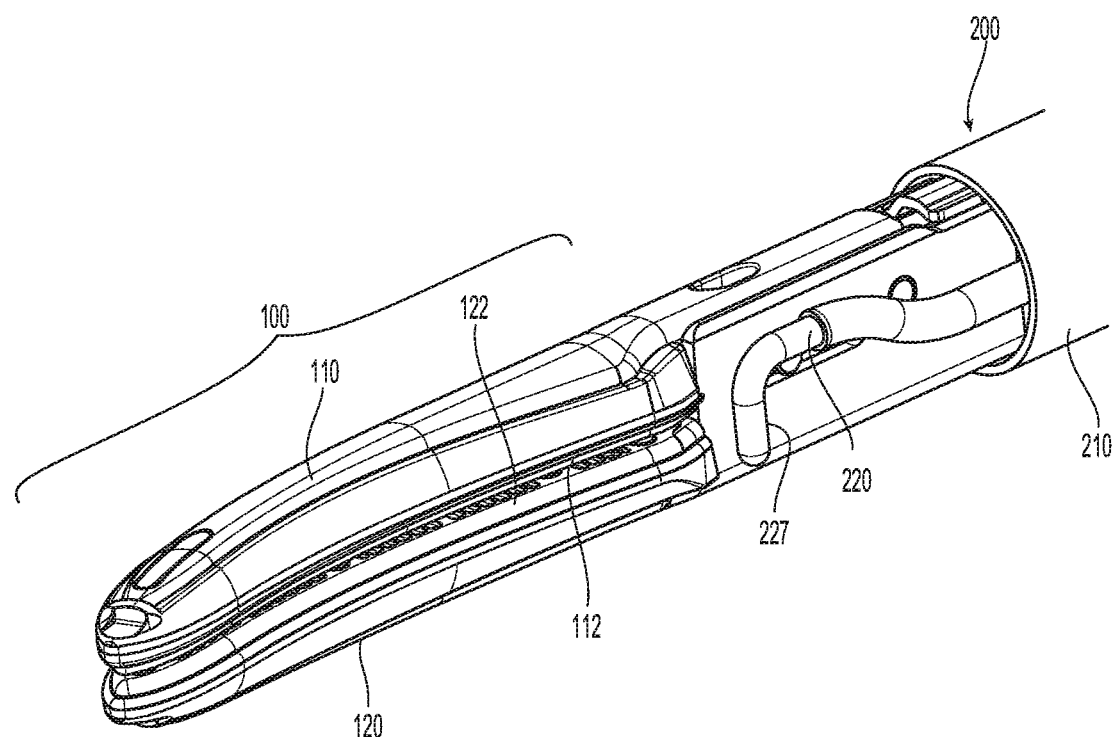
FIG. 2 is an enlarged, perspective view of a distal end portion of the surgical instrument of FIG. 1, wherein a deployable assembly thereof is disposed in a retracted position.
Figure 3:
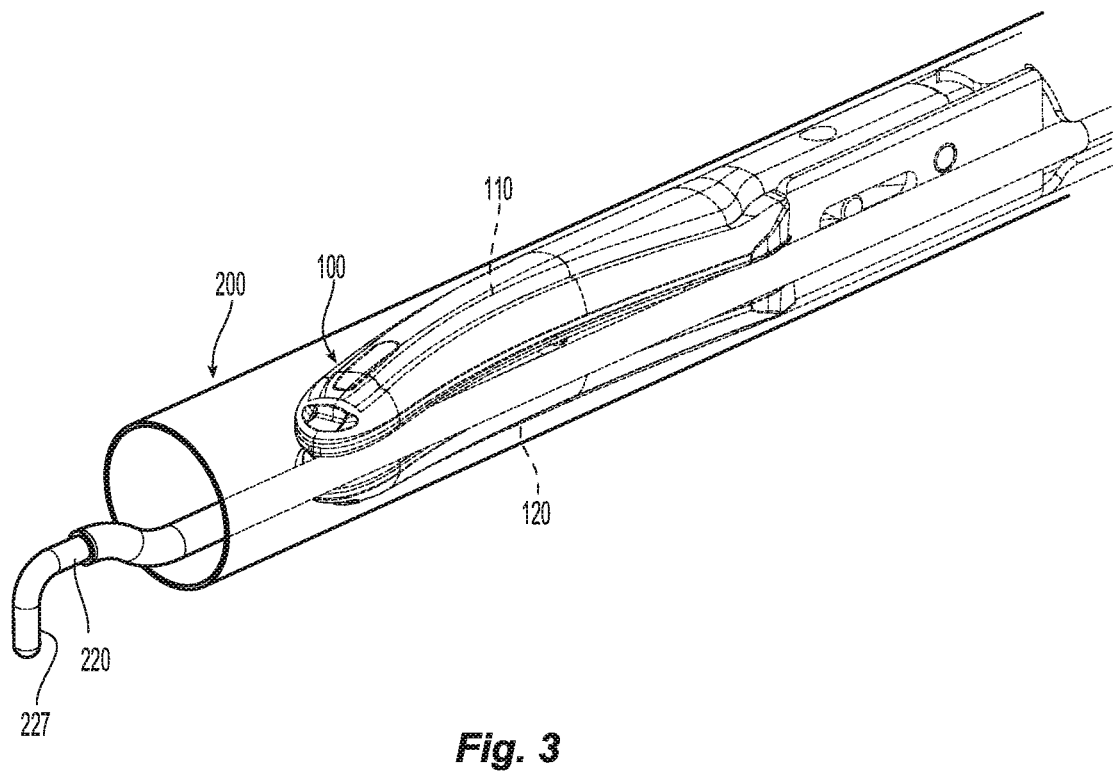
FIG. 3 is an enlarged, perspective view of the distal end portion of the surgical instrument of FIG. 1, wherein the deployable assembly is disposed in a deployed position.
Figure 4:
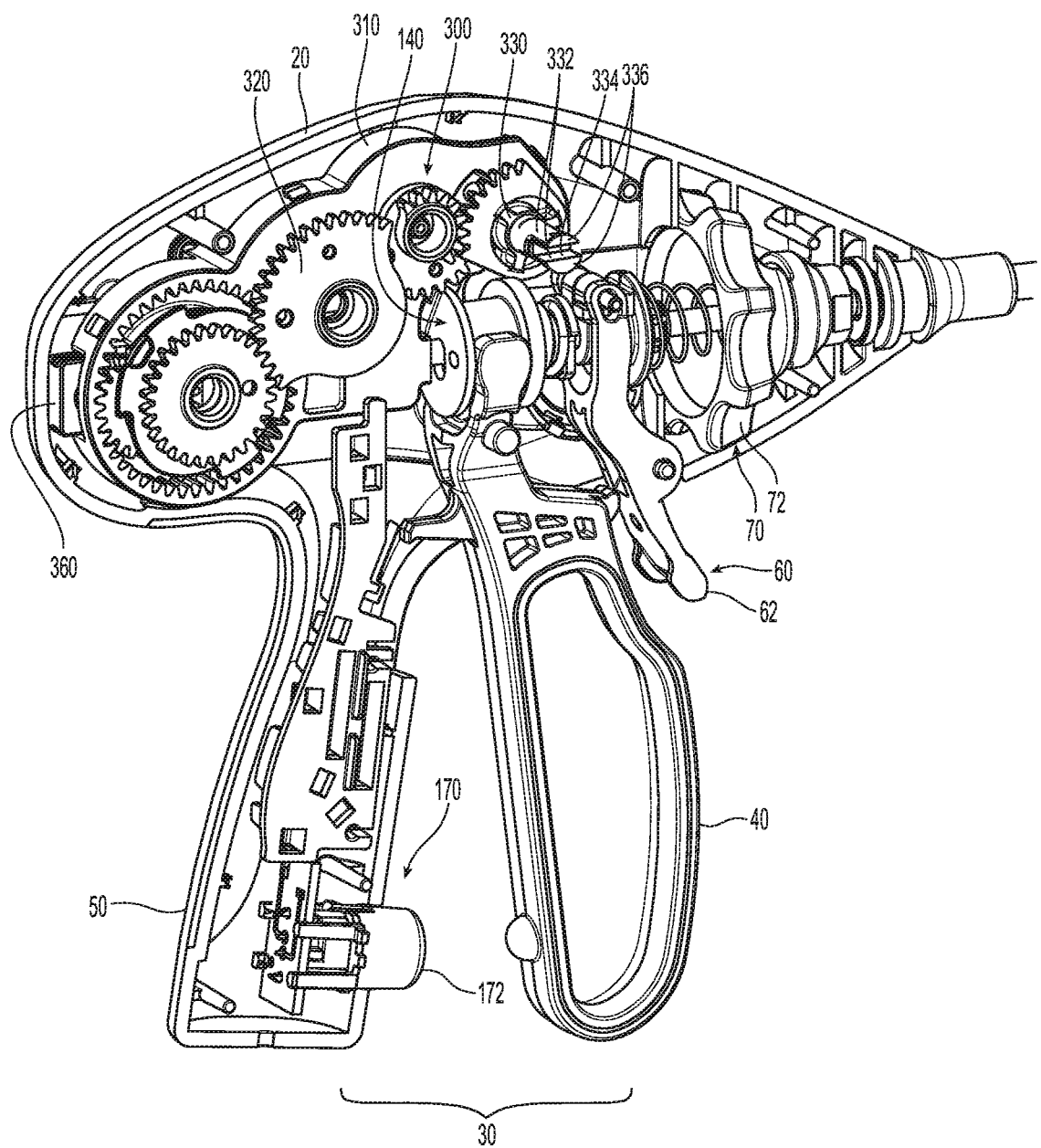
FIG. 4 is a perspective view of a proximal end portion of the surgical instrument of FIG. 1 with portions removed to illustrate the internal working components thereof.

Referring to FIG. 1, a multi-function surgical instrument provided in accordance with the present disclosure is shown generally identified by reference numeral 10. Instrument 10 is configured to operate in both a bipolar mode, e.g., for grasping, treating, and/or mechanically dissecting tissue, and a monopolar mode, e.g., for treating and/or electrically/electromechanically dissecting tissue. Although the present disclosure is shown and described with respect to instrument 10, the tools and methods facilitating reprocessing provided in accordance with the present disclosure are equally applicable for use with any suitable surgical instrument or portion(s) thereof. Obviously, different considerations apply to different instruments; however, the aspects and features of the present disclosure remain generally consistent regardless of the particular instrument provided. For the purposes herein, instrument 10 is generally described.

With reference to FIGS. 1-4, instrument 10 generally includes a housing 20, a handle assembly 30, a trigger assembly 60, a rotation assembly 70, an elongated shaft assembly 80, an end effector assembly 100, a drive assembly 140, a knife assembly (not shown), bipolar and monopolar activation assemblies 170, 180, respectively, a monopolar assembly 200, and a deployment and retraction mechanism 300. Instrument 10 also includes an electrosurgical cable 400 that connects instrument 10 to a generator (not shown) or other suitable power source. Electrosurgical cable 400 includes wires (not shown) extending therethrough that have sufficient length to extend through housing 20 and/or elongated shaft assembly 80 in order to provide energy to at least one of the electrically-conductive surfaces 112, 122 of jaw members 110, 120, respectively, of end effector assembly 100, e.g., upon activation of bipolar activation switch 172 of bipolar activation assembly 170 in the bipolar mode of operation. Similarly, one or more of the wires of electrosurgical cable 400 extends through housing 20 and/or elongated shaft assembly 80 in order to provide energy to monopolar assembly 200, e.g., upon activation of either of the monopolar activation switches 182 of monopolar activation assembly 180 in the monopolar mode of operation.

Elongated shaft assembly 80 extends distally from housing 20 and supports end effector assembly 100 at a distal end thereof. End effector assembly 100 includes opposing jaw members 110, 120 pivotably coupled to one another. Each of the jaw members 110, 120 includes an electrically-conductive surface 112, 122 adapted to connect to the source of energy and defines a bipolar configuration in use wherein surface 112 is charged to a first electrical potential and surface 122 is charged to a second, different electrical potential such that an electrical potential gradient is created for conducting energy between surfaces 112, 122 and through tissue grasped therebetween for treating tissue. Bipolar activation switch 172 of bipolar activation assembly 170 (FIG. 1) is operably coupled between the source of energy (not shown) and surfaces 112, 122 via one or more wires (not shown), thus allowing the surgeon to apply bipolar energy to surfaces 112, 122 of jaw members 110, 120, respectively, of end effector assembly 100 during a bipolar mode of operation.

Handle assembly 30 includes a movable handle 40 and a fixed handle 50. Movable handle 40 is movable relative to fixed handle 50 between an initial position, wherein movable handle 40 is spaced-apart from fixed handle 50, and a compressed position, wherein movable handle 40 is compressed towards fixed handle 50. Drive assembly 140 is operably coupled between handle assembly 30 and end effector assembly 100 to enable pivoting of jaw member 110 relative to jaw member 120 between the spaced-apart position and the approximated position in response to actuation of movable handle 40 between the initial position and the compressed position.

Continuing with reference to FIGS. 1-4, trigger 62 of trigger assembly 60 is selectively actuatable relative to housing 20 from an un-actuated position to an actuated position. The knife assembly (not shown) is operably coupled to trigger 62 such that actuation of trigger 62 from the un-actuated position to the actuated position translates a knife of the knife assembly from a retracted position, wherein the knife is disposed proximally of jaw members 110, 120, to an extended position, wherein the knife extends at least partially between jaw members 110, 120 and through the knife channel (not shown) defined within jaw members 110, 120 to cut tissue grasped between jaw members 110, 120.

Rotation of rotation wheel 72 of rotation assembly 70 relative to housing 20 effects corresponding rotation of at least a portion of elongated shaft assembly 80, end effector assembly 100, drive assembly 140, the knife assembly, and monopolar assembly 200 relative to housing 20.

Monopolar assembly 200 includes an insulative sheath 210 and an energizable member 220. Insulative sheath 210 is movable relative to end effector assembly 100 between a storage position, wherein insulative sheath 210 is disposed proximally of end effector assembly 100, and a use position, wherein insulative sheath 210 is substantially disposed about end effector assembly 100. Energizable member 220 is coupled to the source of energy (not shown) and monopolar activation assembly 180 (FIG. 1) via one or more wires (not shown) and functions as the active electrode of monopolar assembly 200. Energizable member 220 is movable together with insulative sheath 210 and relative to end effector assembly 100 between a storage position, wherein distal tissue-treating portion 227 of energizable member 220 is positioned more-proximally, and a use position, wherein distal tissue-treating portion 227 of energizable member 220 extends distally from end effector assembly 100 to facilitate treating tissue therewith. Energizable member 220, more specifically, is engaged with insulative sleeve 210 such that energizable member 220 and insulative sleeve 210 move together between their respective storage and use positions (collectively the storage and use positions of monopolar assembly 200). In the use position, insulative sheath 210 serves to electrically insulate end effector assembly 100 from distal tissue-treating portion 227 of energizable member 220, while distal tissue-treating portion 227 extends distally from end effector assembly 100. In the use position, energy may be supplied to distal tissue-treating portion 227 of energizable member 220, e.g., via activation of either of the activation switches 182 of monopolar activation assembly 180 (FIG. 1), for treating tissue in the monopolar mode of operation.

With additional reference to FIGS. 5 and 6A-7B, deployment and retraction mechanism 300 is configured for selectively transitioning monopolar assembly 200 between its storage condition and its use condition. Deployment and retraction mechanism 300 generally includes a gear box 310 mounted within housing 20, a gear assembly 320 operably disposed within gear box 310, a pair of input shafts 330 operably coupled to gear assembly 320 and extending transversely from either side of gear box 310 and outwardly from housing 20 through apertures defined through housing 20, a pair of deployment paddles 340 operably coupled to the input shafts 330, and a slider 360 within housing 20 operably coupling an output of gear assembly 330 with energizable member 220 of monopolar assembly 200 (which, in turn, is engaged with insulative sleeve 210) such that deployment and retraction mechanism 300 is configured to enable both deployment and retraction of monopolar assembly 200 in a push-push manner, e.g., wherein monopolar assembly 200 is both deployed and retracted by pushing either of paddles 340 in the same direction.

Referring to FIG. 5, each input shaft 330 (only one is shown in FIG. 5 as the other is obscured by gear box 310) defines a bifurcated configuration including a pair of spaced-apart arms 332 defining a slot 334 therebetween. Each arm 332 includes a finger 336 disposed at the free end thereof. Fingers 336 extend outwardly in opposite directions in generally perpendicular orientation relative to arms 332. The outer surfaces of fingers 336 may be angled to facilitate assembly of body 342 of paddle 340 onto input shaft 330 while arms 332 are resiliently flexible to enable snap-fit engagement of body 342 of paddle about input shaft 330. Thus, assembly is facilitated while disassembly is not easily achieved.

With reference to FIGS. 6A-7B, each paddle 340 (only one is shown in FIGS. 6A-7B) includes a body 342 and a cover plate 350 and is identical in configuration. Thus, the paddles 340 and components thereof will be detailed below in the singular. Body 342 of paddle 340 defines a hub portion 343 at one end thereof and a manipulation portion 344 at the opposite end thereof. Hub portion 343 defines an aperture 345 therethrough, a first pair of shelves 346 disposed on diametrically-opposing sides of aperture 345 on the outwardly-facing side of body 342, and a second pair of shelves 347 disposed on diametrically-opposing sides of aperture 345 on the inwardly-facing side of body 342. The pairs of shelves 346, 347 are offset 90 degrees relative to one another. Body 342 further includes a recess 348 extending from hub portion 343 towards manipulation portion 344. A window 349 is defined through body 342, within recess 348, towards the grasping-portion-end side of body 342.

Cover plate 350 of paddle 340 includes an outwardly-facing surface 351 and an inwardly-facing surface 352 and includes a hub end portion 353 at one end thereof and a second end portion 354 at a second, opposite end thereof. Hub end portion 353 of cover plate 350 includes a pair of spaced-apart arms 355 extending from inwardly-facing surface 352 of cover plate 350. Each arm 355 includes a finger 356 disposed at the free end thereof. Fingers 356 extend outwardly in opposite directions in generally perpendicular orientation relative to arms 352. The outer surfaces of fingers 356 may be angled to facilitate assembly of cover plate 350 onto body 342 of paddle 340 while arms 355 are resiliently flexible to enable snap-fit engagement of cover plate 350 about body 342 of paddle 340. Thus, assembly is facilitated while disassembly is not easily achieved. Hub end portion 353 of cover plate 350 further includes a boss 357 extending from inwardly-facing surface 352 of cover plate 350 and disposed between spaced-apart arms 355. Boss 357, in the assembled condition, extends into slot 334 to inhibit disengagement of fingers 336 from shelves 346. Cover plate 350 also includes a tab 358 extending from second end portion 354 thereof.

Referring to FIGS. 1 and 4-7B, during manufacture of surgical instrument 10, gear box 310 is enclosed within housing 20 with input shafts 330 extending from gear box 310 outwardly of housing 20 through apertures defined within housing 20. The body 342 of each paddle 340 is engaged about one of the input shafts 330 by inserting paddles 340, without cover plates 350 thereon, about input shafts 330 such that fingers 336 extend through apertures 345 of hub portions 343 of bodies 342 of paddles 340 and snap into engagement on the first pairs of shelves 346 of bodies 342 of paddles 340. Once bodies 342 of paddles 340 are engaged in this manner, cover plates 350 are engaged within recesses 348 of bodies 342 whereby spaced-apart arms 355 of cover plates 350 extend through apertures 345 of hub portions 343 of bodies 342 and into slots 334 defined within input shafts 330 and snap into engagement on the second pairs of shelves 347 of bodies 342 of paddles 340. Further, upon engagement of cover plates 350 within recesses 348 of bodies 342, tabs 358 of cover plates 350 extend through windows 349 of bodies 342 to also secure cover plates 350 towards manipulation portions 344 of bodies 342.

With general reference to FIGS. 1-7B, as a result of the configuration of deployment and retraction mechanism 300, wherein gear box 310 is disposed within housing 20 and paddles 340 are engaged with input shafts 330 externally of housing 20, paddles 340 are required to be disengaged and removed from input shafts 330 before housing 20 can be opened for further disassembly and reprocessing. Further, the above-detailed snap-fit engagements between input shafts 330 and bodies 342 of paddles 340 and between bodies 342 of paddles 340 and cover plates 350 of paddles 340 are not readily disengagable. Accordingly, provided in accordance with the present disclosure and detailed below are tools and methods facilitating reprocessing by enabling efficient and effective removal of paddles 340.

Referring to FIGS. 8A-8D, in embodiments, in order to disengage and remove cover plate 350 from body 342, as shown in FIG. 8A, a pilot hole 500 is drilled into hub end portion 353 of cover plate 350 on-axis with input shaft 330. Thereafter, as shown in FIG. 8B, a set screw 510 is threaded into the pilot hole 500 such that the set screw 510 extends through cover plate 350 but does not extend beyond boss 357. In embodiments, pilot hole 500 may be tapped to facilitate threading of set screw 510 therein. The exposed portion of set screw 510, e.g. the portion not threaded into pilot hole 500 thus provides an on-axis structure capable of being grasped and manipulated. Turning to FIGS. 8C and 8D, this exposed portion of set screw 510, more specifically, is grasped, e.g., using a grasper or other suitable tool (not shown), and pulled away from body 342 of paddle 340 in a direction generally coaxial with the axis of input shaft 330 to thereby forcibly disengage fingers 356 of cover plate 350 from the second pairs of shelves 347 of bodies 342 of paddle 340 and forcibly withdraw tab 358 of cover plate 350 from window 349 of bodies 342, thereby enabling removal of cover plate 350 from body 342.

With reference to FIGS. 8D and 8E, upon re-assembly, once cover plate 350 is re-engaged with body 342, set screw 510 may be threaded into cover plate 350 to be flush or recessed relative to outwardly-facing surface 351 of cover plate 350 and to extend beyond boss 357 on the inwardly-facing surface 352 of cover plate 350. This further threading of set screw 510 drives set screw 510 further inwardly and, more specifically, into slot 334 defined between arms 332 of input shaft 330. As a result, set screw 510 ensures that body 342 of paddle 340 is securely engaged about input shaft 330 and cover plate 350 is securely engaged with body 342, even if portions thereof, e.g., fingers 336, fingers 356, and/or tabs 358, were damaged during disassembly or modification. Set screw 510 also serves to self-tap itself into arms 332 to securely hold the adjacent components together in an assembled condition. Thus, even if some or all of the retention features (e.g., fingers 336, fingers 356, and/or tabs 358) are damaged and/or absent, set screw 510 enables all of the components to maintain engaged with one another. More specifically, set screw 510 holds cover plate 350 to shaft 330 with the body 342 sandwiched therebetween.

In embodiments, an adhesive or other suitable material may be applied on and/or around set screw 510 on the outwardly-facing surface 351 of cover plate 350. In embodiments where the components of input shaft 330 and paddle 340 are undamaged, rather than further threading set screw 510 into cover plate 350, set screw 510 may be removed and the vacant hole 500 (FIG. 8A) filled with an adhesive or other suitable material. In embodiments, another suitable tool such as a flexible barb (not shown) may be utilized in place of set screw 510 to pull cover plate 350 away from body 342 of paddle 340. In other embodiments, set screw 510 may define a greater length such that set screw 510 may initially be driven further through cover plate 350 and urged into contact with input shaft 330 to thereby urge cover plate 350 to disengage from body 342.

Referring to FIGS. 9A-10B, in other embodiments, in order to disengage and remove cover plate 350 from body 342, an access notch 610, 620 is created in the portion of body 342 of paddle 340 defining the outer periphery of recess 348 and/or within the outer periphery of cover plate 350. The access notch 610 may be created at hub portion 343 of body 342 in alignment with a long axis of paddle 340, as illustrated in FIGS. 9A-9C or the access notch 620 may be created at hub portion 343 of body 342 at a position offset from the long axis of paddle 340, as illustrated in FIGS. 10A and 10B. Other suitable positions for creating the access notch 610, 620 about hub portion 343 of body 342 are also contemplated. Access notch 610, 620 may be created using any suitable device or method and, once created, provides access for a pry tool 630 to be inserted into access notch 610, 620 to pry cover plate 350 out of engagement with body 342 of paddle 340. Creating the notch 610, 620 at hub portion 343 allows the pry tool 630 to provide a prying force substantially (e.g., at least 40% of the prying force applied) in a direction parallel to the pivot axis of paddle 340, thus facilitating removal of cover plate 350. With respect to re-assembly, if no portions are damaged during disassembly or modification, re-assembly may proceed similarly as detailed above. However, if portions were damaged during disassembly or modification, an adhesive or other suitable material may be applied to secure cover plate 350 to body 342 of paddle 340 during reassembly.

Figure 11A:
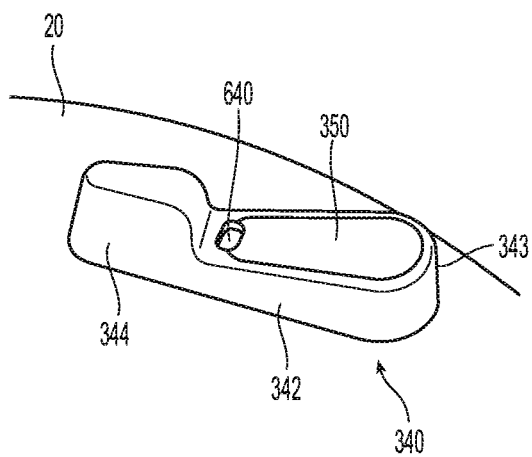
FIGS. 11A and 11B illustrate yet other tools and/or methods of disassembling the cover plate of the paddle from the body thereof.
Figure 11B:
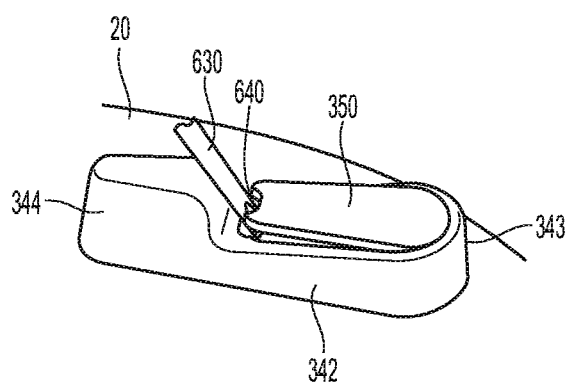

Turning to FIGS. 11A and 11B, access notch 640 may be created at manipulation portion 344 of body 342, removing tab 358 therewith, in alignment with the long axis of paddle 340, and pry tool 630 utilized to disengage cover plate 350 from body 342 of paddle 340. In this approach, it is likely that one or both arms 355 and/or fingers 356 will be damaged during disassembly as the prying force is less in a direction parallel to the pivot axis of paddle 340 and more in an oblique direction. Thus, an adhesive or other suitable material is likely to be needed to secure cover plate 350 to body 342 of paddle 340 during reassembly. In some embodiments, pry tool 630 may be utilized as above, in any suitable position, without first creating an access notch.

The removal of cover plate 350 may be facilitated by and or alternatively performed in other manners such as, for example, temporarily attaching an tool (not shown) to cover plate 350 using an adhesive, bonding agent, adhesive tape, etc., to facilitate removal of cover plate 350. Once cover plate 350 is removed, the tool can be detached therefrom. In another embodiment, a vacuum cup tool (not shown) can be attached to cover plate 350 to facilitate removal. In still another embodiment, a self-drilling screw (not shown) can be used to grasp cover plate 350 to facilitate removal. In yet other embodiments, a thin pry-tool (not shown) can be inserted into the existing gap (without creating a notch) between cover plate 350 and body 342 of paddle 240 to pry cover plate 350 loose. In still yet another embodiment, a sharp tool (not shown) can be used to cut through cover plate 350 or body 342 of paddle 340 to gain grip and then use a prying action to disengage cover plate 350.

Figure 12A:
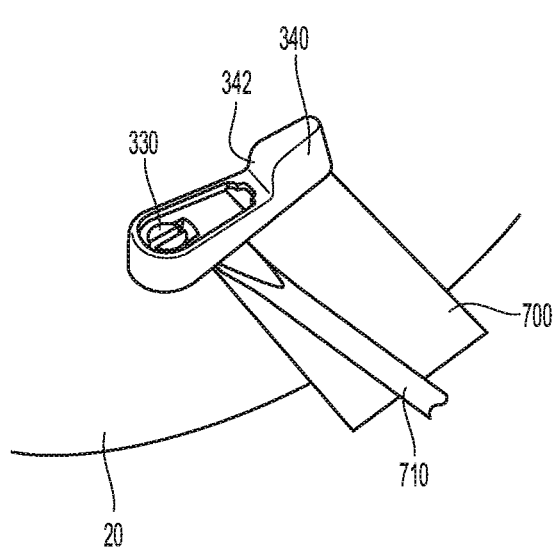
FIGS. 12A and 12B illustrate tools and/or methods of disassembling the body of the paddle from the surgical instrument of FIG. 1.
Figure 12B:
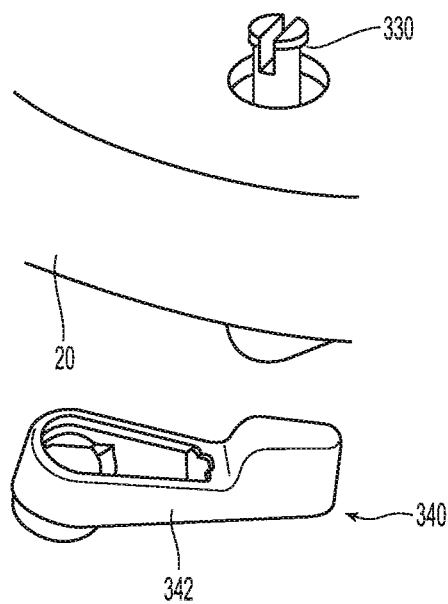

With reference to FIGS. 12A and 12B, once cover plate 350 (FIGS. 8C, 8D, and 9A-11B) is removed from body 342 of paddle 340, body 342 of paddle 340 is removed from input shaft 330 to enable housing 20 to be opened and the internal components therein accessed. With cover plate 350 no longer in position, slot 334 of input shaft 330 is unoccupied, thus allowing arms 332 to flex inwardly to enable body 342 to be disengaged from input shaft 330. In embodiments, as illustrated in FIG. 12A, a protective sheet 700 may optionally be inserted between body 342 of paddle 340 and housing 20 and thereafter a pry tool 710 is inserted between protective sheet 700 and body 342 of paddle 340 adjacent hub portion 343 of body 342. Pry tool 710 is utilized to urge body 342 away from housing 20 such that arms 332 of input shaft 330 are urged inwardly into slot 334, thus disengaging fingers 336 from first shelves 346 and enabling removal of body 342 from input shaft 330. This may be accomplished, where pry tool 710 is a flat-edge instrument, by rotating pry tool 710 about its axis, or in any other suitable manner. Protective sheet 700 protects housing 20 from damage during prying of body 342 off of input shaft 330. Further, in order to prevent moving of housing 20 during prying, housing 20 may be placed in a nest (not shown) to immobilize housing 20. The pry force is provided substantially (e.g., at least 40% of the prying force applied) in a direction parallel to the axis of input shaft 330, thus facilitating removal of body 342. Pressing down on the manipulation portion end of body 342 while manipulating the pry tool 710 may create a three-point bending loading condition in body 342 for maximum leverage, and also serves to trap body 342 from flying away once disengaged from input shaft 330.

Instead of utilizing a pry tool 710 (FIG. 12A), a spreader tool 810 may be utilized to disengage and remove body 342 of paddle 340 from input shaft 330, as illustrated in FIG. 13. Disassembly using spreader tool 810 is otherwise similar to that detailed above with respect to pry tool 700 (FIG. 12A).

Referring to FIG. 14, instead of utilizing a pry tool 710 (FIG. 12A) or a spreader tool 810 (FIG. 13), a lasso loop 910 may be utilized to disengage and remove body 342 of paddle 340 from input shaft 330. Lasso loop 910 may be slipped between body 342 of paddle 340 and housing 20 and slid into position adjacent hub portion 343 of body 342. Thereafter, lasso loop 910 is pulled upwardly, in a direction parallel to the axis of input shaft 330 such that arms 332 of input shaft 330 are urged inwardly into slot 334, thus providing a pulling force in a direction parallel to the axis to disengage fingers 336 from first shelves 346 and enable removal of body 342 from input shaft 330. To facilitate the disengagement of fingers 336 from first shelves 346, a pliers (not shown) may be utilized to pinch arms 332 of input shaft 330 inwardly towards one another prior to lifting of lasso loop 910. Alternatively, with reference to FIG. 15, an insert 1010 may be utilized to surround and urge arms 332 of input shaft 330 inwardly prior to lifting of lasso loop 910, thus facilitating the disengagement of fingers 336 from first shelves 346. In any of the above embodiments for removing bodies 342 of paddles 340, housing 20 may be placed in a nest (not shown) to immobilize housing 20 during removal of bodies 342 of paddles 340.

Turning to FIGS. 16A-16D, another method of removing body 342 of paddle 340 from input shaft 330 includes use of a removal tool 1100. Removal tool 1100 includes an outer shaft 1110, an inner shaft 1120, and a lever 1130. Lever 1130 is pivotably coupled to inner shaft 1120 by way of a pivot pin 1132 and is operably coupled to outer shaft 1110 by way of a rack and pinion arrangement 1134. As a result of this configuration, pivoting lever 1130 relative to inner shaft 1120 urges outer shaft 1110 to slide about inner shaft 1120. Inner shaft 1120 further includes a base platform 1122.

Figure 16A:
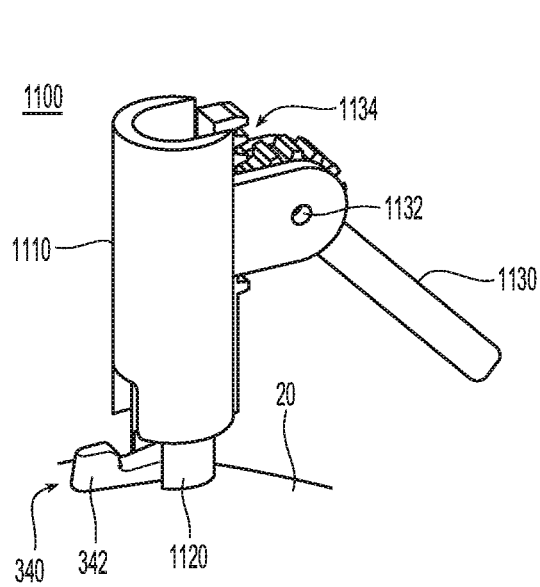
FIGS. 16A-16D illustrate other tools and/or methods of disassembling the body of the paddle from the surgical instrument of FIG. 1.
Figure 16B:
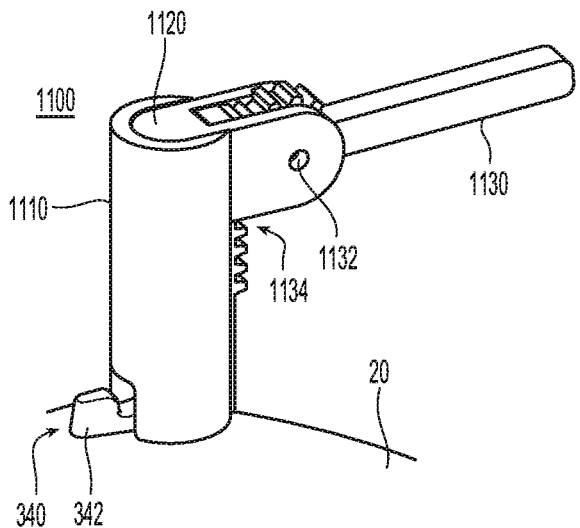
Figure 16C:
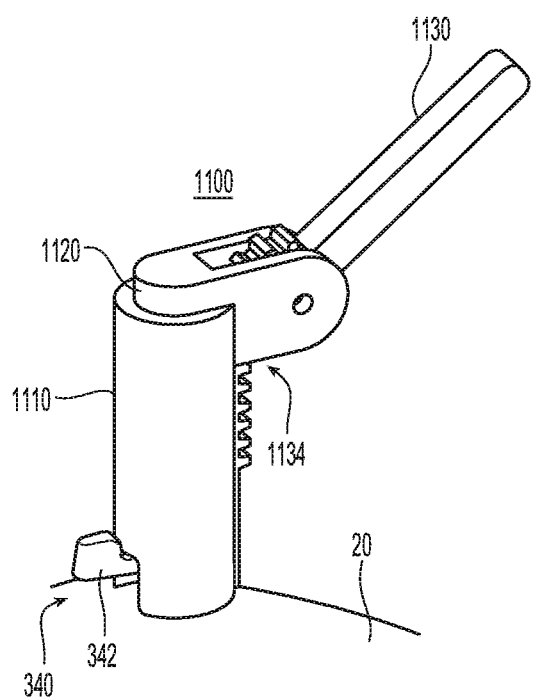
Figure 16D:
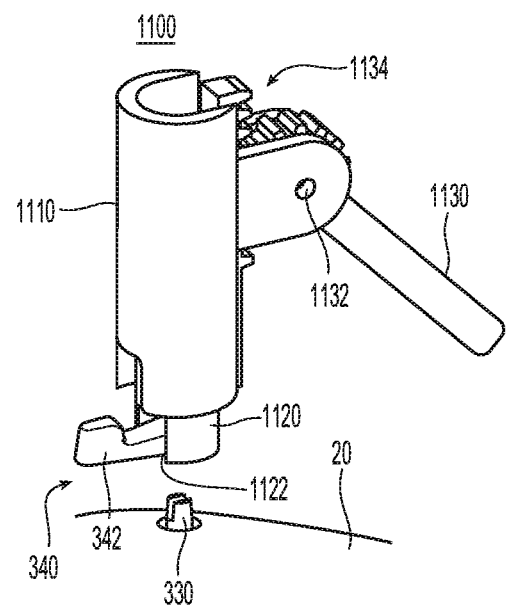

In use, with initial reference to FIG. 16A, with lever 1130 positioned such that base platform 1122 of inner shaft 1120 extends from outer shaft 1110, removal tool 1100 is positioned such that base platform 1122 is disposed between body 342 of paddle 340 and housing 20. Once this position has been achieved, lever 1130 is pivoted, as illustrated in FIGS. 16B and 16C, such that outer shaft 1110 translates over inner shaft 1120 towards housing 20. Upon further pivoting of lever 1130, outer shaft 1110 eventually contacts housing 20 and, via the relative movement between outer shaft 1110 and inner shaft 1120, urges body 342 of paddle 340 away from housing 20 under a force parallel to the axis of input shaft 330, thereby disengaging body 342 of paddle 340 from input shaft 330. Once body 342 of paddle 340 is disengaged, as shown in FIG. 16D, lever 1130 may be returned to the initial position to permit removal of body 342 of paddle 340 from removal tool 1100. In embodiments, instead of a handheld tool, removal tool 1100 may be an automated such as, for example, part of a disassembly line. In such embodiments, when an instrument is moved to the appropriate station along the disassembly line, removal tool 1100 is slid into position and lever 1130 is actuated to remove paddle 340 from housing 20. Additionally or alternatively, removal tool 1100 may incorporate a tool like insert 1010 or other suitable tool to urge arms 332 of input shaft 330 inwardly prior to lifting body 342 of paddle 340, thus facilitating the disengagement of fingers 336 from first shelves 346 and removal of body 342 of paddle 340 from input shaft 330.

With body 342 of paddle 340 removed from input shaft 330, housing 20 may be separated into housing halves and opened, thus allowing the internal components thereof to be removed for cleaning/disinfection, modification, refurbishment, and/or replacement before re-assembly and sterilization. Once housing 20 is reassembled, body 342 of paddle 340 may be reassembled onto input shaft 330. The re-assembly of body 342 of paddle 340 onto input shaft 330 is similar to the assembly thereof, detailed above, with the exception that an adhesive or other suitable material, or structural component such as a set screw, may be utilized to secure body 342 of paddle 340 on input shaft 330 and/or cover plate 350 onto body 342, if portions thereof are damaged during disassembly.

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A method of disassembling a surgical instrument, comprising:
    obtaining a surgical instrument including a housing, an input shaft defining an axis and extending from the housing, and a paddle engaged with the input shaft and configured to pivot about the axis;
    disengaging a cover plate of the paddle from a body of the paddle by providing a force to the cover plate substantially in a direction parallel to the axis, wherein disengaging the cover plate includes engaging a set screw with the cover plate and manipulating the set screw to provide the force to the cover plate; and
    disengaging the body from the input shaft by providing a force to the body substantially in a direction parallel to the axis.
2. The method according to claim 1, wherein disengaging the body from the input shaft includes engaging a removal tool with the body and actuating a lever of the removal tool to provide the force to the body.

3. The method according to claim 2, wherein engaging the removal tool with the body includes engaging an inner shaft of the removal tool with the body, and wherein actuating the lever of the removal tool slides an outer shaft of the removal tool relative to the inner shaft and into contact with the housing to provide the force to the body.

4. The method according to claim 3, wherein the lever of the removal tool is pivotably coupled to the inner shaft and coupled to the outer shaft via a rack and pinion, and wherein actuating the lever includes pivoting the lever relative to the inner shaft.

5. The method according to claim 3, wherein the removal tool further includes an insert disposed therein, the insert urging arms of the input shaft inwardly prior to providing the force to the body to facilitate removal of the body from the input shaft.

6. The method according to claim 1, wherein the set screw is engaged with the cover plate in alignment with the axis.

7. The method according to claim 1, wherein engaging the set screw includes drilling a pilot hole through the cover plate and threading the set screw into the pilot hole.

8. A method of disassembling a surgical instrument, comprising:

obtaining a surgical instrument including a housing, an input shaft defining an axis and extending from the housing, and a paddle engaged with the input shaft and configured to pivot about the axis;

disengaging a cover plate of the paddle from a body of the paddle by providing a force to the cover plate substantially in a direction parallel to the axis; and disengaging the body from the input shaft by providing a force to the body substantially in a direction parallel to the axis, wherein disengaging the body from the input shaft includes engaging a removal tool with the body and actuating a lever of the removal tool to provide the force to the body, wherein engaging the removal tool with the body includes engaging an inner shaft of the removal tool with the body, and wherein actuating the lever of the removal tool slides an outer shaft of the removal tool relative to the inner shaft and into contact with the housing to provide the force to the body.

* * * * *